United States Patent [19]
Yasumura
[11] Patent Number: 4,917,684
[45] Date of Patent: Apr. 17, 1990

[54] PROTECTIVE COVER FOR INLET/OUTLET PORTS OF THE PLASTIC BAG USED FOR MEDICAL PURPOSE

[75] Inventor: Isao Yasumura, Hiroshima, Japan

[73] Assignee: Japan Medical Supply Co., Ltd., Hiroshima, Japan

[21] Appl. No.: 388,759

[22] Filed: Aug. 1, 1989

Related U.S. Application Data

[63] Continuation of Ser. No. 88,861, Aug. 24, 1987, abandoned.

[30] Foreign Application Priority Data

Sep. 1, 1986 [JP] Japan ............ 61-134760
Dec. 4, 1986 [JP] Japan ............ 61-187266

[51] Int. Cl.⁴ ............ A61B 19/00
[52] U.S. Cl. ............ 604/468; 128/DIG. 24
[58] Field of Search ............ 104/408–410, 104/4–6, 257, 262, 319, 317, 322–326; 248/95, 97, 99; 128/767–768, DIG. 24; 206/633, 628, 620, 616, 571, 438–440, 601, 605, 607, 609; 604/905, 411–416; 220/265, 266, 268, 269, 276, 359; 664/403–407

[56] References Cited

U.S. PATENT DOCUMENTS 2,997,043 8/1961 Flynn ............ 604/263
3,343,541 9/1962 Bellamy, Jr. ............ 604/408
3,788,374 1/1974 Saijo ............ 604/408
4,234,026 11/1980 Bayham ............ 621/408
4,314,025 2/1982 McCue ............ 435/2
4,556,842 11/1985 Cummings ............ 604/408

FOREIGN PATENT DOCUMENTS 52-42634 9/1977 Japan .
58-168332 11/1983 Japan .
59-100431 7/1984 Japan .

*Primary Examiner*—Max Hindenburg
*Assistant Examiner*—K. M. Reichle
*Attorney, Agent, or Firm*—Kramer, Brufsky & Cifelli

[57] ABSTRACT

A protective cover for sealing ports mounted to a plastic bag is disclosed. The ports can be observed through the protective cover and the protective cover can be easily removed from the port with one hand. A tab is welded on one side of the protective cover and is tapered toward the hub of the port. The tab is welded to the protective cover by heat and has a flat, smooth surface so that it becomes transparent or semi-transparent.

11 Claims, 3 Drawing Sheets

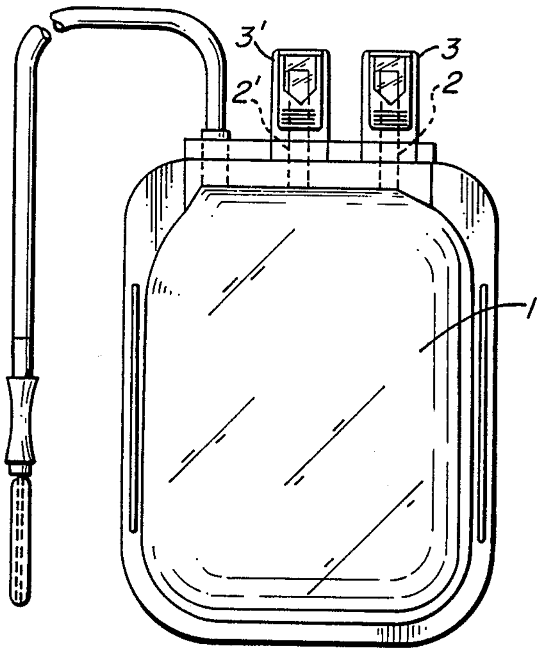
FIG. 1
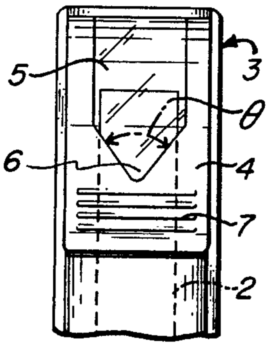
FIG. 2A
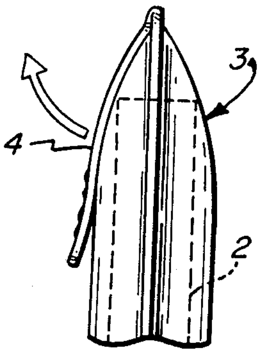
FIG. 2B
FIG. 3A
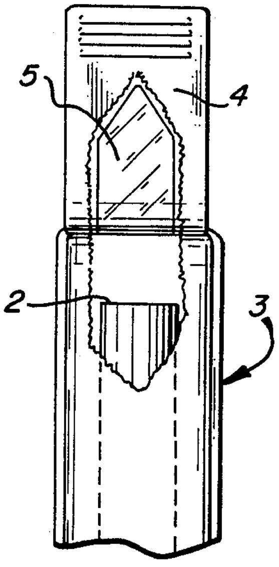
FIG. 3B
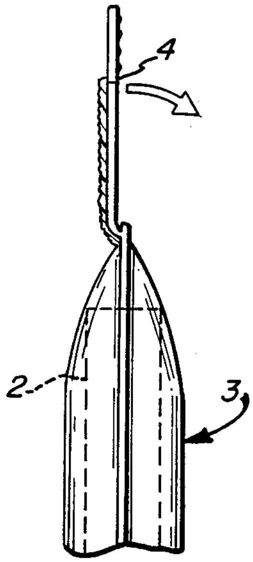

PROTECTIVE COVER FOR INLET/OUTLET PORTS OF THE PLASTIC BAG USED FOR MEDICAL PURPOSE

This application is a continuation of application Ser. No. 07/088,861, filed Aug. 24, 1987, now abandoned.

BACKGROUND OF INVENTION

This invention relates to a protective cover for sealing the inlet/outlet ports of a plastic bag, such as a blood bag or solution bag, used for medical patient infusions. The purpose of the protective cover is to seal the ports and maintain the contents as well as the ports sterile prior to their use.

When the plastic bag is being used, the protective cover is pulled apart in order to expose the port. The conventional type of blood bag, as described in U.S. Pat. No. 4,314,025, has two tabs provided at the edge of the protective cover. The cover can be pulled apart from each side by pulling the tabs along the welded line and then tearing the cover from the port.

Japanese Utility Model Publication No. 42634/77 discloses the method whereby the tab mounted on one side of the cover is welded to the protective cover. In addition, a V-shaped part is welded to the protective cover. When the cover is being removed by pulling on the tabs, it will readily tear in a "V" shape. This operation may be performed and completed with a single hand. Also, Japanese Utility Model Application Laid-Open Nos. 168332/83 and 100431/84 disclose that a tab welded to one side of the protective cover can be removed with a single hand so as to unseal the port.

The conventional plastic bag used for medical purposes is usually made up of two soft plastic sheets welded together along their peripheral edges. In order to prevent the sheets from sticking together, the surface of each sheet has been finely roughened. As a result of this treatment, the soft plastic sheets develop a cloudiness which makes it difficult to see through them and observe the contents of the bag.

Also, in the case of the conventional plastic cover openable with a single hand, the port can be viewed through the two plastic sheets, that is to say, the protective cover and the tab. The two sheets cause even more difficulty in observing the ports of the bag. Due to this condition, it is virtually impossible to detect a latent or obvious defect or abnormality which might exist in the port(s).

OBJECTS OF INVENTION

It is an object of this invention to provide a protective cover for sealing ports of a plastic bag which keeps the ports in a sterile condition.

It is another object of this invention to provide a protective cover for sealing ports of a plastic bag through which the ports may be easily observed.

It is still another object of this invention to provide a protective cover for sealing ports of a plastic bag which can be easily removed.

BRIEF DESCRIPTION OF THE DRAWINGS

The objectives and benefits of this invention may be fully understood after an evaluation of the explanation along with the attached drawings which follow. The following, then, is an explanation of each attached drawing.

FIG. 1 is the front view of a plastic bag fitted with ports and the newly invented protective cover for those ports.

FIG. 2(A) is a front view of the protective cover in accordance with the present invention.

FIG. 2(B) is a side view of a protective cover in accordance with the present invention.

FIG. 3(A) is a front view of a tab partially removed from a protective cover in accordance with the present invention.

FIG. 3(B) is a side view of a tab partially removed from a protective cover in accordance with the present invention.

DESCRIPTION OF INVENTION

As shown in FIG. 1, the new protective covers 3 and 3' protect ports 2 and 2' mounted to the top of the plastic bag 1. The plastic bag is formed of two sheets of finely roughened, soft plastic material which are welded together along their edges. The ports 2 and 2' must be kept sealed and sterilized until used. For use, the ports are unsealed by removing the protective covers. The top of the ports are then exposed so that they may be pierced by a coupler or needle for either adding other medicines to or extracting the contents from the bag.

Figure 4A:
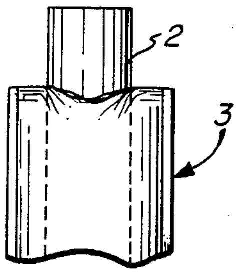
FIG. 4(A) is a front view of a protective cover having the tabs pulled away from the port in accordance with the present invention.
Figure 4B:
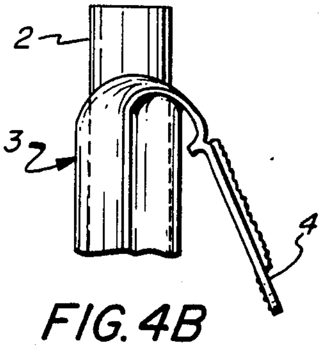
FIG. 4(B) is a side view of a protective cover wherein the tab has been pulled away from the port in accordance with the present invention.

As shown in FIGS. 2(A) and 2(B), a tab 4 is welded on one side of the protective cover. The end 6 of the welded part 5 is pointing in the direction of the port base and is tapered off on that end. All other surfaces of the welded parts are preferably either rectangular or square in shape. The die which is used for welding the tab to the protective cover has a flat, smooth surface which makes the tab transparent or semi-transparent. Consequently, it is easy to observe the port through the protective cover 3 and the tab 4. The tab may be pulled up in the direction of the arrow, as shown in FIG. 2(B), for removing the protective cover and thereby unsealing the port 2. The tab is torn off the bag by pulling from the tip end 6 of the tapered welded part 5 along the peripheral, tapered edges of the weld in order to gain access to the port opening as shown in FIGS. 3(A) and 3(B). The top of the port 2 may be exposed by continuing to pull the tab in the direction of the arrow as shown in FIG. 3(B) until the top of the port is fully exposed, as shown in FIGS. 4(A) and 4(B).

Figure 7:
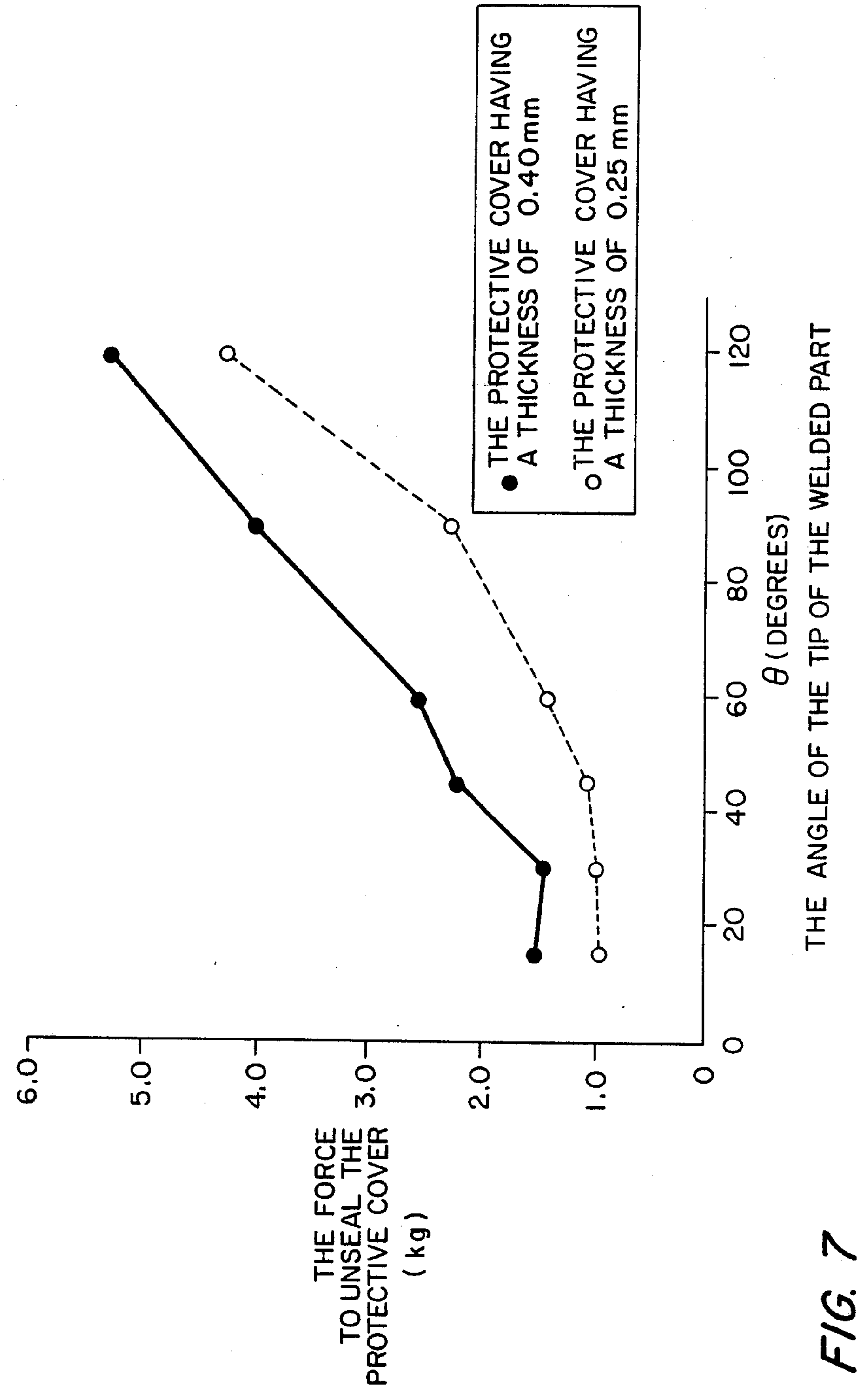
FIG. 7 is a diagram showing the relationship of the force to unseal the protective cover of the present invention and the angle of the tip of the welded part.

Usually, when performing the protective cover removal operation, the greatest amount of force must be exerted at the beginning of the procedure. With this invention, a relatively low amount of force is required and the unsealing may be accomplished quickly due to the fact that the tip 6 of the welded part 5 is sharply tapered so that the tearing force may be concentrated at the initial tearing point. The angle of the tip of the welded part closely correlates with the force required to tear off the protective cover when the port is being unsealed. As shown in FIG. 7, the unsealing may be accomplished with less force when the angle $\ominus$ of the tip 6 of the welded part is less than 90 degrees. The recommended angle $\ominus$ should be about 60 degrees.

Rather than have the same thickness of plastic material for the sheet of plastic used to form the protective cover 3 and the tab 4, it is recommended that the plastic sheet used for the tab be thicker than the plastic sheet used for the protective cover. Then, the protective cover is certain to be torn off the bag 1 without tearing the tab off the cover. Usually, soft plastic material such as Polyvinylchloride (PVC) or an Ethylene-Vinyl Acetate copolymer is the preferred plastic sheet material used for the protective cover or the tab. The thickness range forming the protective cover for the sheet is recommended to be from about 0.2 mm to about 0.4 mm. The thickness range recommended for the tab is from about 0.4 mm to about 0.8 mm. Unsealing may be accomplished with much less force when the protective cover is thin, as seen in FIG. 7. Welding of the tab to the protective cover may be accomplished by conventional, well known welding methods including high frequency heating. Also, the end of the tab has corrugations 7, as shown in FIG. 2(*a*), to facilitate a secure, firm hold with the fingers.

Figure 5:
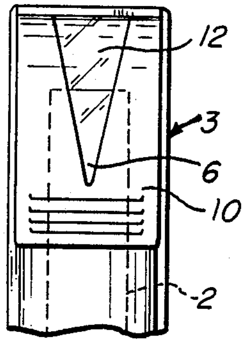
FIG. 5 is a front view of a second embodiment of the protective cover in accordance with the present invention.
Figure 6:
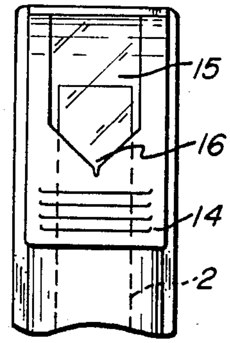
FIG. 6 is a front view of a third embodiment of the protective cover in accordance with the present invention.

FIGS. 5 and 6 show other embodiments of the present invention. For example, in FIG. 5, the tab 10 includes a welded part 12 which corresponds to part 5 of FIG. 2(*a*). The welded part or welded area 12 is tapered away from the base of the port and provides a sufficient opening area so that the port 2 is adequately exposed. FIG. 5 shows the entire welded part as wedge shaped.

The design of the tab 14, as shown in FIG. 6 is basically the same as tab 3 shown in FIG. 2. However, the angle of the wedge shaped section of the welded part 15 is sharpest at its tip 16 and gradually widens towards the top of the port 2.

The cited patents and patent applications are incorporated in their entireties by reference herein.

These, then, are the descriptions and explanations of the preferred embodiments of the invention. Also, it is possible to modify the design thereof limited to modifications which preserve the basic concept of the invention.

What is claimed is:

1. A bag adapted for medical use, comprising:

a plastic bag having one or more projecting ports;

plastic cover means attached to said bag for covering said one or more projecting ports; and plastic tab means affixed to said cover means for tearing an opening area in said plastic cover means to expose said one or more projecting ports, said tab means having a welded portion with a weld area welded to said cover means, the weld area of said welded portion corresponding in area to the opening area in the plastic cover means.

2. The bag of claim 1 wherein the weld area of said welded portion has first and second ends, said first end being tapered and disposed closest to said bag to reduce the force needed to tear the welded portion from said cover means.

3. The bag of claim 2 wherein the weld area of said welded portion is tapered substantially to a point at said first end to initially concentrate the tearing force at the point.

4. The bag of claim 3 wherein the angle of the tapered and of the weld area is less than about 90°.

5. The bag of claim 4 wherein the angle of the tapered end of the weld area is about 60°.

6. The bag of claim 4 wherein the welded portion is substantially wedge shaped.

7. The bag of claim 3 wherein the second end of the weld area of said welded portion opposite said tapered end of the weld area is substantially rectangular.

8. The bag of claim 3 wherein the tapered end of the weld area is sharpest at the first end and gradually widens towards the second end.

9. The bag of claim 3 wherein the plastic tab means is thicker than the plastic cover means whereby the cover means is torn without tearing the tab means.

10. The bag according to claim 9 wherein the plastic cover means has a thickness of from 0.2 mm to 0.4 mm and the plastic tab means has a thickness of from 0.4 mm to 0.8 mm.

11. The bag of claim 1 wherein said tab means has a flat, smooth, relatively transparent surface.

* * * * *